(12) United States Patent
Inskeep

(10) Patent No.: US 11,039,519 B2
(45) Date of Patent: Jun. 15, 2021

(54) DOOR MOUNTED SANITIZER LIGHT

(71) Applicant: Mathew Inskeep, Highland Beach, FL (US)

(72) Inventor: Mathew Inskeep, Highland Beach, FL (US)

(*) Notice: Subject to any disclaimer, the term of this patent is extended or adjusted under 35 U.S.C. 154(b) by 0 days.

(21) Appl. No.: 14/571,692

(22) Filed: Dec. 16, 2014

(65) Prior Publication Data
US 2016/0249436 A1    Aug. 25, 2016

Related U.S. Application Data

(60) Provisional application No. 61/917,534, filed on Dec. 18, 2013.

(51) Int. Cl.
*H05B 47/105*     (2020.01)
*H05B 47/16*      (2020.01)
*E05B 1/00*       (2006.01)
*A61L 2/10*       (2006.01)

(52) U.S. Cl.
CPC ............. *H05B 47/105* (2020.01); *A61L 2/10* (2013.01); *E05B 1/0069* (2013.01); *H05B 47/16* (2020.01); *Y02B 20/40* (2013.01)

(58) Field of Classification Search
CPC . A61L 2/10; A61L 2/18; E05B 1/0069; A61N 5/0624; B08B 9/023
USPC ...... 250/492.1, 455.11, 493.1, 338.3, 504 R; 315/149, 360, 362; 422/24, 186.3
See application file for complete search history.

(56) References Cited

U.S. PATENT DOCUMENTS

| | | | | |
|---|---|---|---|---|
| 4,710,634 A * | 12/1987 | Brookes | .................... | A61L 2/10 16/412 |
| 7,175,807 B1 * | 2/2007 | Jones | .................... | E05B 1/0069 250/455.11 |
| 7,989,779 B1 * | 8/2011 | Ray | .......................... | A61L 2/10 250/455.11 |
| 8,581,522 B2 * | 11/2013 | Inskeep | .................... | A61L 2/10 315/149 |
| 9,339,570 B2 * | 5/2016 | Whitney | ................... | A61L 2/10 |
| 2006/0076743 A1 * | 4/2006 | Dunser | ................... | B08B 9/023 280/33.992 |
| 2011/0291995 A1 * | 12/2011 | Shr | ......................... | A61L 2/10 345/176 |
| 2012/0305804 A1 * | 12/2012 | Goldman | .............. | E05B 1/0069 250/492.1 |
| 2013/0279966 A1 * | 10/2013 | Roberts | ................. | E05B 1/0069 401/207 |
| 2014/0048724 A1 * | 2/2014 | Marshall | .................. | A61L 2/10 250/492.1 |

* cited by examiner

*Primary Examiner* — David A Vanore
(74) *Attorney, Agent, or Firm* — McHale & Slavin, P.A.

(57) ABSTRACT

A mountable multiple angle sanitizing light for a door handle with the ability to be powered by batteries or ac mains. Preferably, ultraviolet light is used to disinfect the particular area of the door handle. A motion detection system can also be incorporated to regulate safety procedures and for controlling a light shut-off time, time off, and light illumination time.

9 Claims, 3 Drawing Sheets mounting arm pull plate push plate

DOOR MOUNTED SANITIZER LIGHT

This application claims the benefit and priority of U.S. Ser. No. 61/917,534

STATEMENT REGARDING FEDERALLY SPONSORED RESEARCH

The invention was not made under government contract nor was funded grant money used to fund the research

FIELD OF INVENTION

This invention is in the field of decontamination devices utilizing ultra violet light.

SUMMARY OF THE INVENTION

The present invention is a Door Mounted Sanitizer Light that effectively provides germicidal effect to any parts of the door structure or handles that may come in contact with the person opening, closing, or passing through the door. In general, the Door Mounted Sanitizer incorporates an ultraviolet (UV) light used to disinfect this particular area. Depending upon the features incorporated, the sanitizer (UV) light may be turned on to illuminate a push plate from the outside surface, or to illuminate a push plate from an internal illuminator through the glass plate, or may illuminate a handle from an illuminating ultraviolet source that is projected from the housing of the fixture. It may incorporate a motion detection system that will regulate safety procedures that will control a light shut-off time, time off, and light illumination time to insure safety from skin or tissue burns. These control times may be adjusted to apply optimum on times, off times, sanitizing times, and safety off times depending on the characteristic conditions of the application. The fixture may be powered from internally mounted replaceable batteries or from house power fed through the door with insulated wire.

BACKGROUND OF THE INVENTION

It is well known that surface areas of any type carry a variety of pathogens that are potentially harmful to human beings. Our hands are one of the ways these pathogens can be carried and passed on to the human body through eating or biting one's fingernails. The invention can be used to assist in destroying pathogens that come into contact during everyday activities such as the touching of a door handle. It is impossible to constantly scrub door surfaces to ensure they are sanitized. The present invention provides a way to ensure surfaces are repeatedly cleaned minimizing human exposure to potentially harmful pathogens. The ultra violet light is well known to decontaminate surfaces when properly exposed to the light for a certain period of time. This invention is a decontamination device that kills pathogens before transmission to the human body by stopping them at the source of transmission. Ultraviolet lamps are used to sterilize workspace and tools in biology and medical facilities. Commercially available low pressure vapor lamps emit a frequency spectrum that coincides within the germicidal effectiveness curve. The Ultraviolet-C's effectiveness is directly related to intensity and exposure time.

DETAILED DESCRIPTION OF THE INVENTION

Figure 2:
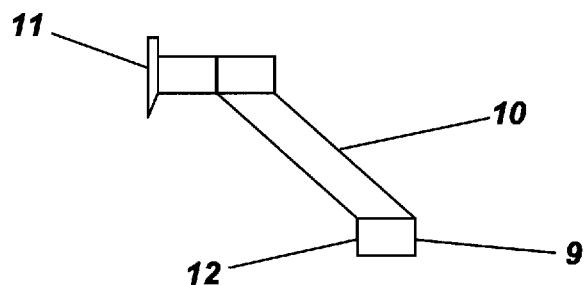
FIG. 2 is a representation of the door sanitizer mounting arm.

There are a variety of options that may be incorporated into the Door Mounted Sanitizer Light to make it an effective germicidal fixture. The Door Mounted Sanitizer Light may be used to illuminated non-porous push plate on which the ultraviolet light is projected from a mounting bracket (FIG. 2).

Figure 3:
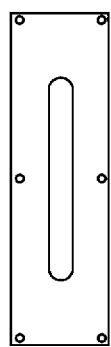
FIG. 3 is an image of a push plate with a handle.
Figure 4:
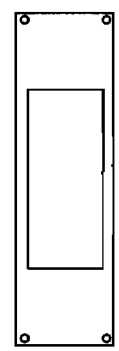
FIG. 4 is an image of the push plate without a handle but with a rear glass.
Figure 5:
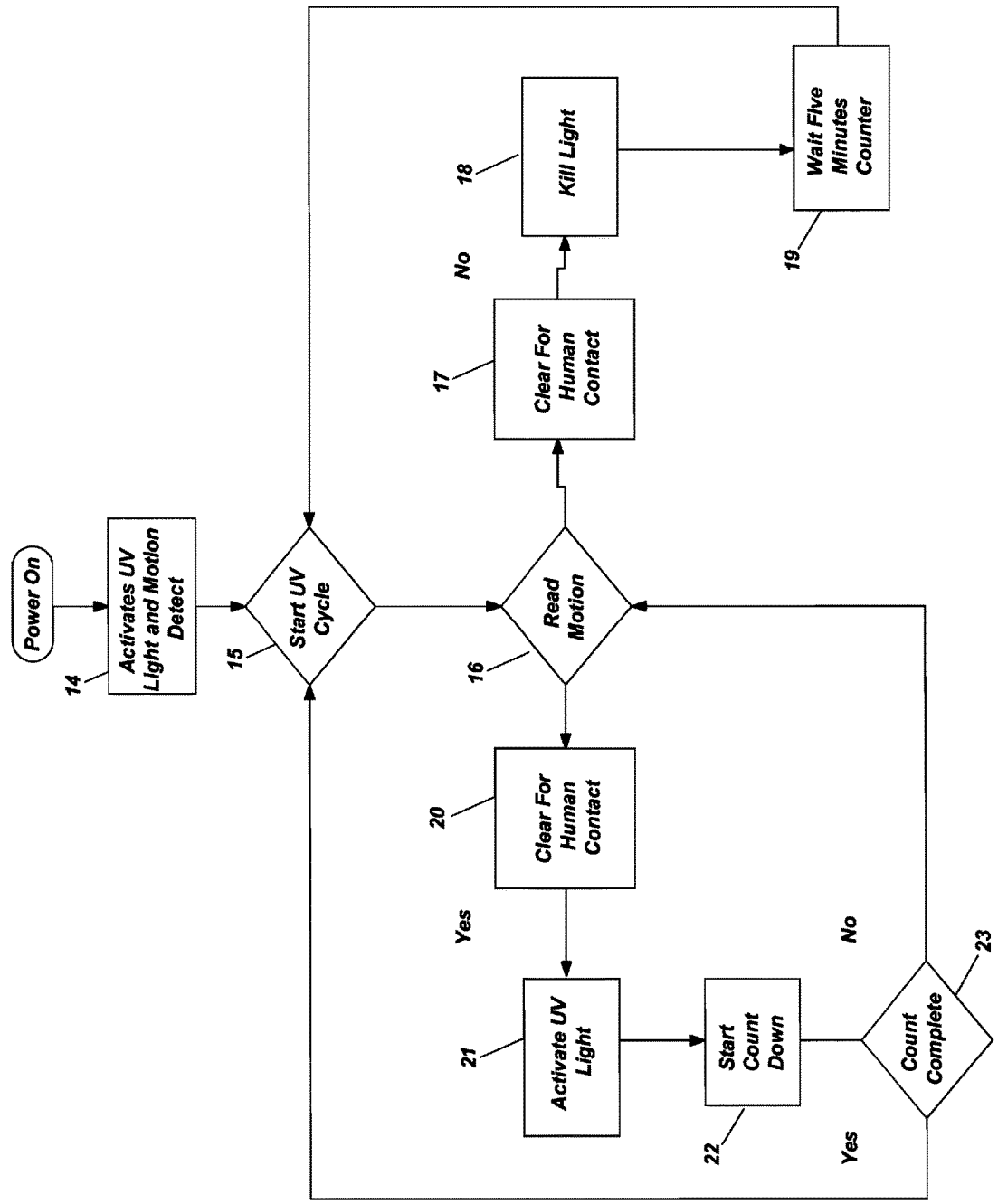
FIG. 5 is a logic function flow chart of a sanitizing cycle.

The Door Mounted Sanitizer Light may also be illuminated from the rear of the push plate through the glass cover of the push plate (FIG. 4). The ultraviolet light may also be projected onto the door handle (FIG. 3), or other similar door fixture that may be utilized for the door operation. A motion detector (FIG. 1) may be incorporated to control the detection of surface contact and a control and timing unit (FIG. 1) 4 that will control the length of time the ultraviolet light is on, versus the length of time the ultraviolet light is turned off. This motion detector (FIG. 1) 5 also can start the sequence for timed intervals for optimum germicidal effects of the parts of the door handles/plates of the operating times of the door. The power to operate any of these options can be supplied by replaceable battery cells (FIG. 1) 6 mounted in any of the enclosures. Power may also be supplied through the door through insulated wire from "house" (FIG. 1) 8 power with the necessary conversion to applicable DC power (FIG. 1) 7.

The goal of the present invention is to maximize the disinfection on door fixtures that are constantly exposed to microorganism when people are periodically opening and closing the doors by pushing (FIG. 3) or pulling (FIG. 4) means.

The present invention addresses the following factors to maximize the disinfection process. First, with this new invention the distance between the ultraviolet (UVC) lamp and the pathogen is controlled, secondly, the invention achieves good light exposure using a high intensity (UVC) lamp and finally it controls the duration of exposure. The apparatus is a self-contained structure as shown by the main system on FIG. 1. The invention will be permanently affixed to the door and automatically powered by the internal monitoring circuit. The self-contained structure could use a housing method such as the mounting arm enclosure and mechanism on (FIG. 2). This permanent attachment will maximize the effectiveness of the disinfection process, by having a localized and controlled distance to destroy the microorganism residing in the door area (FIG. 3), Depending upon the features incorporated, the present invention may illuminate a push plate (FIG. 4) from an internal illuminator through the glass plate, or may illuminate a handle (FIG. 3). The main component that achieves decontamination will be the Ultraviolet (UVC) light also known as a germicidal lamp. Germicidal lamps are mainly used in the disinfection and sterilization processes on flat surfaces. They give off light at the short wavelength of the light spectrum which is harmful to microorganism pathogens. As a result, the area is disinfected when exposed to (UV) rays. The complete Door Mounted Sanitizer Light will consist of energy radiated from an ultraviolet (UV) light source such as that on a germicidal bulb (FIG. 1) 1, or germicidal lamp (FIG. 1) 2 or other ultraviolet (UV) source (FIG. 1) 3 with similar characteristic. Depending on the surface area to be sterilized and market availability, different type of bulbs can be used as part of the complete system. For simplicity and consistency moving forward, I will refer to ultraviolet (UV) light as commercially known Ultraviolet-C (UVC) light. The UVC light emits a blue spectrum of light to help expose the surface area to be cleaned. UVC light operates in a spectrum between 200-280 nm, known as a short wave germicidal, in which, the germicidal peak is accomplished between 250 nm 280 nm which is the most light absorbed by the sample. The invention combines this already existing technology and integrates a control and timing circuit (FIG. 1) 4 in combination with a motion sensor (FIG. 1) 5 to detect when an individual comes in direct contact with the door surface and immediately engages in the sanitizing process thereafter. The direct benefit is to disinfect an area that may contain microorganisms by disrupting their life cycle by exposing them to (UVC) rays before an individual comes in contact with such area. The main system (FIG. 1) contains various circuits such as the control and timing circuit (FIG. 1) 4 which essentially controls the length of time the (UVC) light will be powered after the motion sensor (FIG. 1) 5 sends a signal to activate the germicidal lamp. The length of time that the (UVC) light will stay powered will depend on the surface area to be disinfected.

As previously stated, distance, time of exposure and light intensity are key factors to the success of disinfecting the desired area. The functionality of the motion sensor (FIG. 1) 5 is to detect any movement within the vicinity of the door opening or closing fixture, and then trigger a signal to the control and timing circuit (FIG. 1) 4, to turn on the germicidal lamp (FIG. 1) (UV) bulb.

The powering circuit of the Door Mounted Sanitizer can be supplied by two methods: First, replaceable cells (FIG. 1) 6 that can be integrated into the battery compartment in the mounting arm (FIG. 2) 10 fixture. The second method, will be to supply power via AC mains household or commercial line voltage (FIG. 1) 8 including the applicable rectification circuit (FIG. 1) 7.

Figure 1:
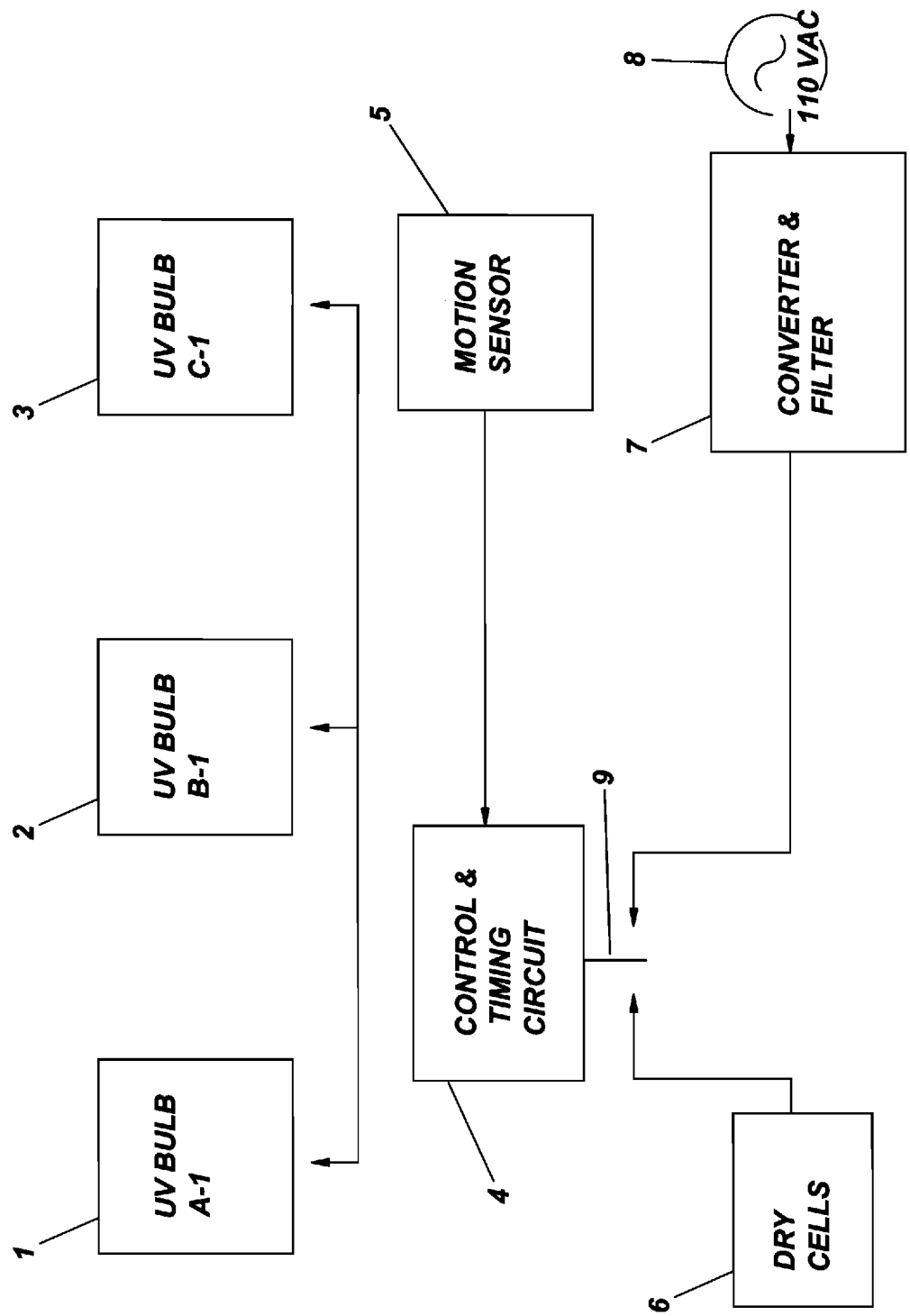
FIG. 1 is a block diagram showing the basic controls and circuitry of the sanitizer including several of the options that may be included in this sanitizer.

FIG. 4 describes the logic operation of the control and timing circuit previously described on FIG. 1. Initially, the Door Mounted Sanitizer will be powered by integrated battery(s) or via AC mains (refer to FIG. 1). Once the unit receives the power from either source, the invention will activate the UV bulb and motion detection sensor 14. This is accomplished by the signal received from the internal control and timing circuit (FIG. 1). After both of these controls are active, the timing circuit will begin a sanitizing cycle 15. During this process, the processor will perform a safety check by reading the motion sensor signal 16. The motion sensor signals will read and will clear the sanitizing process to commence depending on any human contact to the surface to be sanitized. During the first condition, the signal to the processor will detect for any motion 16 from the sensor and this will deliver a signal back to the control unit (FIG. 1) not to activate and kill light 18 for a period of at least five minutes if any human contact 17 is detected. The internal counter 19 will count down for the pre-determined amount of time before looping back to the starting cycle 15 and try again. This signal will loop back to the start of the UV cycle 15 and will continue to loop around until a new condition is met or power is removed from supply. During the second condition, the signal to the processor will detect for any motion 16 from the sensor and if no motion human motion is detected 20, the control circuit will activate the UV light 21 and commence the sanitizing cycle. During the sanitizing cycle, there is an internal count down 22 that checks and verifies if the pre determine count is completed 23. If the internal count is not complete, the processor will read again the motion 16 verified once again there is still no human contact and continue with sanitizing cycle. During the sanitizing cycle, the count complete 23 will loop around and read motion sensor 16 on a pre-determine amount of time before continuing the sanitizer cycle. This process will minimized any extended human exposure to UV light if they happen to become in contact with the touch surface during the sanitizing process. The control and timing circuit (FIG. 1), are real time active components of the invention, driven by an internal processor that inputs and outputs the decision criteria just described,

What is claimed is:

1. A system for sanitizing a fixture of a door, comprising:
   a door having a front surface and a back surface;
   a glass push plate fixture having an outer surface and a rear surface, said fixture secured to either said door front surface or said door back surface;
   at least one ultraviolet light source positioned to illuminate through said glass push plate rear surface such that when activated the at least one ultraviolet light source provides ultraviolet light that is used directly or indirectly for sanitizing said fixture;
   a motion sensor configured to detect movement in an area adjacent to said door and disable the at least one ultraviolet light source; and
   a control and timing circuit in communication with the at least one ultraviolet light source and in communication with the motion sensor; the control and timing circuit programmed to receive information from the motion sensor when the motion sensor detects movement in the area and the control and timing circuit programmed to activate the at least one ultraviolet light source for a previously configured period of time when movement in the area has ceased; and
   a power source for powering the control and timing circuit.

2. The system for sanitizing a fixture of said door of claim 1 wherein the power source is one or more replaceable batteries battery cell.

3. The system for sanitizing a fixture of said door of claim 1 wherein the power source is an AC current source in communication with a rectification circuit.

4. The system for sanitizing a fixture of said door of claim 1 wherein the ultraviolet light source is a germicidal bulb.

5. The system for sanitizing a handle or a fixture of said door of claim 1 including a handle secured to said glass push plate that is illuminated by the at least one ultraviolet light source when the ultraviolet light source is activated by the control and timing circuit.

6. The system for sanitizing a fixture of said door of claim 1 wherein the ultraviolet light source is a germicidal lamp.

7. A method for sanitizing a fixture of a door, comprising the steps of:
   a. automatically detecting by a motion detector any motion made within a vicinity of a door;
   b. triggering a signal to a control and timing circuit by the motion detector when motion is detected by the motion detector;
   c. activating at least one ultraviolet light source by the control and timing circuit upon receipt of the signal from the motion detector; and d. directly projecting ultraviolet light from the ultraviolet light source through a rear surface of a glass push plate of the door.

8. The method for sanitizing a fixture of said door of claim 7, further comprising the step of programming the control and timing circuit with a specific period of time for the ultraviolet light source to be activated each time a triggering signal is received from the motion detector.

9. The method for sanitizing a fixture of said door of claim 8, further comprising the step of deactivating the ultraviolet light source at and end of the specific period of time.

\* \* \* \* \*